United States Patent [19]

Aschwanden et al.

[11] Patent Number: 4,461,906
[45] Date of Patent: Jul. 24, 1984

[54] PYRROLIDINE 2-ONE DERIVATIVES

[75] Inventors: Werner Aschwanden, Ettingen; Emilio Kyburz, Reinach, both of Switzerland

[73] Assignee: Hoffmann-La Roche Inc., Nutley, N.J.

[21] Appl. No.: 172,607

[22] Filed: Jul. 28, 1980

[30] Foreign Application Priority Data

Aug. 9, 1979 [CH] Switzerland .......................... 7308/79
Jun. 20, 1980 [CH] Switzerland .......................... 4755/80

[51] Int. Cl.³ ................ C07D 207/273; C07D 407/12; A61K 31/404
[52] U.S. Cl. .................................. 548/406; 548/543; 548/544; 548/517; 424/274
[58] Field of Search .............. 260/326.5 FL; 548/543, 548/544, 517, 406

[56] References Cited

U.S. PATENT DOCUMENTS 4,239,770 12/1980 Kyburz et al. ...................... 424/274

FOREIGN PATENT DOCUMENTS 845099 2/1977 Belgium .

OTHER PUBLICATIONS

Giurgea et al., "Prog. Neuro-psychopharmac", vol. 1, pp. 235-247, (1977).
Faragher et al., Chem. Abst., vol. 86, (1977), 5393r.

1976 Merck Index #7282 Merc. & Co., Rahway, N.J., listed alphabetically under "Piracetam".

Primary Examiner—Paul M. Coughlan, Jr.
Assistant Examiner—D. B. Springer
Attorney, Agent, or Firm—Jon S. Saxe; Bernard S. Leon; Frank P. Hoffman

[57] ABSTRACT

1-Substituted-2-pyrrolidinones of the formula

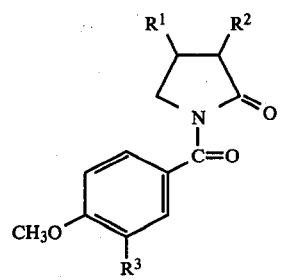

wherein one of $R^1$, $R^2$ and $R^3$ represents hydroxy and the remaining substituents represent hydrogen, are capable of counteracting cerebral insufficiency produced experimentally in animal tests. They can be used therapeutically in the control or prevention of cerebral insufficiency or in the improvement of intellectual capacity. They can be manufactured from novel intermediates and can be processed to provide medicaments.

8 Claims, No Drawings

PYRROLIDINE 2-ONE DERIVATIVES

DESCRIPTION OF THE INVENTION

The present invention relates to pyrrolidine derivatives. More particularly, the invention is concerned with 1-substituted-2-pyrrolidinones of the general formula

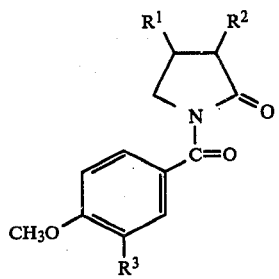

wherein one of $R^1$, $R^2$ and $R^3$ represents hydroxy and the other two represent hydrogen.

These compounds are novel and possess valuable pharmacodynamic properties.

Objects of the present invention are compounds of formula I per se and as pharmaceutically active substances, the manufacture of these compounds and intermediates in the manufacture of these compounds, medicaments containing a compound of formula I and the manufacture of such medicaments, as well as the use of compounds of formula I in the control or prevention of cerebral insufficiency.

Formula I hereinbefore embraces three compounds, namely 1-(p-methoxybenzoyl)-3-hydroxy-2-pyrrolidinone, 1-(p-methoxybenzoyl)-4-hydroxy-2-pyrrolidinone and 1-(3-hydroxy-4-methoxybenzoyl)-2-pyrrolidinone. 1-(p-Methoxybenzoyl)-3-hydroxy-2-pyrrolidinone and 1-(p-methoxybenzoyl)-4-hydroxy-2-pyrrolidinone each contain an asymmetric carbon atom; the present invention embraces not only the optically uniform enantiomeric forms of these two compounds, but also mixtures thereof (especially the racemates). (R)-1-(p-Methoxybenzoyl)-3-hydroxy-2-pyrrolidinone is especially preferred; the corresponding (R,S) compound is also preferred.

The pyrrolidine derivatives of formula I hereinbefore can be manufactured in accordance with the invention by (a) removing the protecting group from a pyrrolidine derivative of the general formula

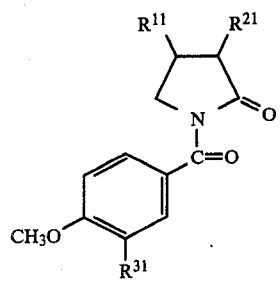

wherein one of $R^{11}$, $R^{21}$ and $R^{31}$ represents a protected hydroxy group and the other two represent hydrogen, or (b) reducing a pyrrolidine derivative of the general formula

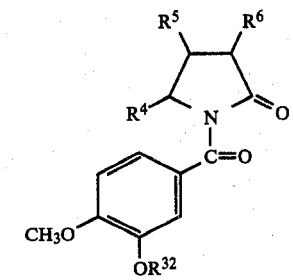

wherein one of $R^4$ and $R^6$ represents hydrogen and the other together with $R^5$ represents a second carbon-carbon bond and $R^{32}$ represents hydrogen or a reductively cleavable protecting group.

According to embodiment (a) of the foregoing process, pyrrolidine derivatives of formula I can be manufactured by removing the protecting group from a pyrrolidine derivative of formula II. As the protecting groups there are, of course, suitable only those which can be cleaved off by methods in which these protecting groups are selectively removed without affecting the other structural elements present in the molecule. The removal of the protecting group from the pyrrolidine derivatives of formula II is carried out according to methods known per se, whereby, of course, the nature of the protecting group to be removed must be taken into consideration when choosing the method to be used and care must be taken that only the protecting group is selectively removed without affecting other structural elements present in the molecule.

Formula II hereinbefore embraces firstly compounds of the general formula

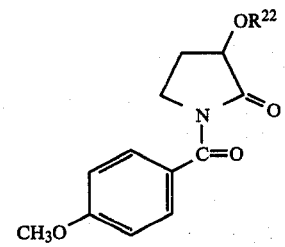

wherein $R^{22}$ represents a protecting group, secondly compounds of the general formula

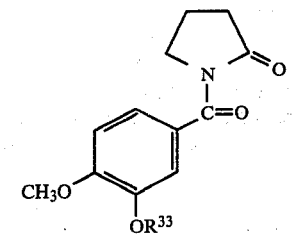

wherein $R^{23}$ represents a protecting group, and thirdly compounds of the general formula

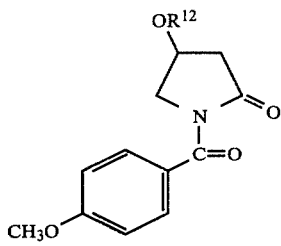

wherein $R^{12}$ represents a protecting group.

Suitable as protecting groups in the compounds of formula IIa (denoted by $R^{22}$) are, for example, readily cleavable alkyl and aralkyl groups such as substituted trityl groups (e.g. p-methoxytrityl, p,p'-dimethoxytrityl or p,p',p'''-trimethoxytrityl) and the like; readily cleavable metal-organic groups, especially trialkylsilyl groups such as trimethylsilyl, and the like; readily cleavable acetal and ketal protecting groups such as hexahydropyran-2-yl, 4-methoxyhexahydropyran-4-yl and the like; readily cleavable acyl groups such as acetyl, chloroacetyl, trifluoroacetyl, methoxyacetyl, phenoxyacetyl, benzyloxycarbonyl, trichloroethoxycarbonyl, tribromoethoxycarbonyl, benzoylformyl and the like; etc.

Methods for the removal of the groups mentioned earlier as examples of protecting groups denoted by $R^{22}$ in compounds of formula IIa are described in the literature and are accordingly familiar to a person skilled in the art. For example, the aforementioned mono-, di- and trimethoxytrityl groups can be cleaved off by treatment with 80% acetic acid at room temperature, the trimethylsilyl group can be cleaved off by treatment with dilute hydrochloric acid in tetrahydrofuran or the like, the hexahydropyran-2-yl group and the 4-methoxyhexahydropyran-4-yl group can be cleaved off under mild acid aqueous conditions (e.g. by means of 0.1 normal hydrochloric acid), the acetyl group can be cleaved off by means of esterase enzymes, the chloroacetyl group can be cleaved off by means of thiourea/pyridine, the trifluoroacetyl group can be cleaved off by means of methanol, the methoxyacetyl and the phenoxyacetyl group can be cleaved off by means of methanolic ammonia, the benzyloxycarbonyl group can be cleaved off by catalytic hydrogenation (e.g. over palladium/carbon), the trichloroethoxycarbonyl and the tribromoethoxycarbonyl group can be cleaved off by means of zinc/copper in glacial acetic acid at room temperature and the benzoylformyl group can be cleaved off by treatment with aqueous pyridine at room temperature.

Suitable as protecting groups in the compounds of formula IIb (denoted by $R^{33}$) are, for example, readily cleavable alkyl groups such as tert.butyl and the like; readily cleavable aralkyl groups such as benzyl and the like; readily cleavable metal-organic groups, especially trialkylsilyl groups such as trimethylsilyl and the like; readily cleavable acetal and ketal protecting groups such as hexahydropyran-2-yl and the like; readily cleavable acyl groups such as fluorenecarbonyl, benzyloxycarbonyl, trichloroethoxycarbonyl, tribromoethoxycarbonyl and the like.

Methods for the cleavage of the groups mentioned earlier as examples of protecting groups denoted by $R^{33}$ in compounds of formula IIb are described in the literature and are accordingly familiar to a person skilled in the art. Thus, for example, the benzyl and the benzyloxycarbonyl group can be cleaved off by catalytic hydrogenation (e.g. over palladium/carbon), the tert.butyl, the trimethylsilyl and the hexahydropyran-2-yl group can be cleaved off under mild acid conditions, the fluorenecarbonyl group can be cleaved off by means of UV-light and the trichloroethoxycarbonyl and the tribromoethoxycarbonyl group can be cleaved off by heating in methanol or by means of zinc/copper in glacial acetic acid.

Suitable as protecting groups in the compounds of formula IIc (denoted by $R^{12}$) are only those groups for which no elimination with formation of a carbon-carbon double bond in the 5-membered heterocycle has to be expected (i.e. acyl groups are not suitable). $R^{12}$ preferable represents a trialkylsilyl group such as trimethylsilyl and the like. Methods for the cleavage of such groups are described in the literature and are accordingly familiar to a person skilled in the art. Thus, for example, the trimethylsilyl group can be cleaved off by treatment with dilute hydrochloric acid in tetrahydrofuran or the like.

According to embodiment (b) of the foregoing process, the compound of formula I in which $R^1$ and $R^2$ represents hydrogen and $R^3$ represents hydroxy, i.e. 1-(3-hydroxy-4-methoxybenzoyl)-2-pyrrolidinone, can be manufactured by reducing a compound of formula III hereinbefore. The compounds of formula III contain in the 5-membered heterocycle a double bond which, depending on the meanings of $R^4$, $R^5$ and $R^6$, is present either in the 3,4-position or in the 4,5-position. It is possible to use mixtures of two compounds of formula III which differ with respect to the position of this double bond. When $R^{32}$ represents a reductively cleavable protecting group, then this group is, for example, a benzyl group, a benzyloxycarbonyl group or the like. It will, of course, be appreciated that the reduction of a compound of formula III in which $R^{32}$ represents a reductively cleavable protecting group should be carried out using only those methods which bring about the reduction of the double bond in the 5-membered heterocycle and the removal of the reductively cleavable protecting group in one operation.

Reduction methods which are suitable for embodiment (b) of the present process are described in the literature and are accordingly familiar to a person skilled in the art. It will, of course, be appreciated that there can be used only those methods which selectively reduce the double bond in the 5-membered heterocycle and remove a protecting group which may be present without affecting other structural elements present in the molecule. Preferably, the reduction of the compounds of formula III is carried out by means of catalytically activated hydrogen in an organic solvent which is inert under the reduction conditions, palladium, platinum and the like coming into consideration as the hydrogenation catalysts and, for example, ethyl acetate, alcohols (such as methanol, ethanol or the like), ethers (such as tetrahydrofuran or the like) etc coming into consideration as the solvents.

The starting materials of formulae II and III hereinbefore are novel and are also objects of the present invention.

Compounds of formula II in which $R^{21}$ represents a protected hydroxy group and $R^{11}$ and $R^{31}$ represent hydrogen, i.e. compounds of formula IIa, can be prepared, for example, by appropriately acylating a pyrrolidine derivative of the general formula

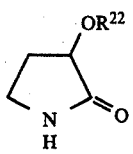

wherein $R^{22}$ has the significance given earlier,
in the 1-position, i.e. replacing the hydrogen atom in the 1-position of a compound of formula IV by a p-methoxybenzoyl group. This can be carried out using methods which are generally known for such acylations. The acylation agent used is a sufficiently reactive derivative of p-methoxybenzoic acid, especially a reactive imidazolide or halide of this acid (preferably p-methoxybenzoyl chloride).

The acylation of a compound of formula IV with p-methoxybenzoyl chloride is conveniently carried out by firstly treating the compound of formula IV with a base capable of removing the hydrogen atom on the nitrogen atom in the 1-position (e.g. with butyl lithium) and then reacting with p-methoxybenzoyl chloride. It is also possible to use the compound of formula IV in the form of a reactive derivative in which a readily cleavable group, especially a trialkylsilyl group such as 1-trimethylsilyl, is present on the nitrogen atom in the 1-position; in this case the protecting groups $R^{22}$ can only be those groups which are not affected under the conditions of the acylation.

The compounds of formula IV can, in turn, be prepared, for example, from 3-hydroxy-2-pyrrolidinone by introducing the desired protecting groups; the molecule for the introduction of the protecting groups vary depending on their nature, but are familiar to a person skilled in the art. For example, a benzyloxycarbonyl group can be introduced by means of chloroformic acid benzyl ester and a chloroacetyl group can be introduced by means of chloroacetyl chloride.

Certain compounds of formula IV can also be prepared from 4-amino-2-hydroxybutyric acid using methods which bring about in one operation cyclisation and introduction of the desired protecting group. Thus, for example, 3-(trimethylsilyloxy)-2-pyrrolidinone can be prepared by reacting 4-amino-2-hydroxybutyric acid in the presence of small amounts of trimethylchlorosilane with hexamethyldisilazane or with bis(trimethylsilyl)urea or with bis(trimethylsilyl)acetamide.

On the other hand, it is also possible to prepare compounds of formula IIa from 4-(p-methoxybenzoylamino)-2-hydroxybutyric acid which, in turn, can be prepared by appropriately acylating 4-amino-2-hydroxybutyric acid (for example, by means of p-methoxybenzoyl chloride). Thus, for example, in the treatment of 4-(p-methoxybenzoylamino)-2-hydroxybutyric acid with acetic acid anhydride there is brought about in one operation cyclisation and introduction of the protecting group, i.e. there is obtained a compound of formula IIa in which $R^{22}$ represents acetyl. Examples of other reagents with which the 4-(p-methoxybenzoylamino)-2-hydroxybutyric acid can be converted in one operation into a compound of formula IIa are chloroacetic acid anhydride, methoxyacetic acid anhydride, trifluoroacetic acid anhydride, hexamethyldisilazane and the like; in the resulting compound of formula IIa $R^{22}$ represents, depending on the reagent used, chloroacetyl or methoxyacetyl or trifluoroacetyl or trimethylsilyl or the like.

Furthermore, it is also possible to cyclise derivatives of 4-(p-methoxybenzoylamino)-2-hydroxybutyric acid, the hydroxy group of which is protected, to give corresponding compounds of formula IIa; for the preparation of such derivatives of 4-(p-methoxybenzoylamino)-2-hydroxybutyric acid, derivatives of 4-amino-2-hydroxybutyric acid, the hydroxy group of which is already protected by the desired protecting group (and which can be readily prepared according to methods known per se), are acylated at the amino group with a sufficiently reactive derivative of p-methoxybenzoic acid, for example with p-methoxybenzoyl chloride.

The compounds of formula IIa have an asymmetric carbon atom in the 3-position of the 5-membered heterocycle. The relevant stereochemical relationships determine the stereochemical relationships in the corresponding compound of formula I in which $R^2$ represents hydroxy and $R^1$ and $R^3$ represent hydrogen, i.e. 1-(p-methoxybenzoyl)-3-hydroxy-2-pyrrolidinone, which can be manufactured from the compounds of formula IIa. The stereochemical relationships in the 3-position of the 5-membered heterocycle of the compounds of formula IIa are, in turn, determined by the intermediates and/or methods used in the preparation of the compounds of formula IIa. It will be clear to a person skilled in the art how, having regard to the relationships just described, optically active or racemic 1-(p-methoxybenzoyl)-3-hydroxy-2-pyrrolidinone can be manufactured in accordance with the invention.

Thus, for example, (R)-1-(p-methoxybenzoyl)-3-hydroxy-2-pyrrolidinone can be manufactured by acylating (R)-4-amino-2-hydroxybutyric acid by means of p-methoxybenzoyl chloride, converting the resulting (R)-4-(p-methoxybenzoylamino)-2-hydroxybutyric acid by means of chloroacetic acid anhydride into (R)-1-(p-methoxybenzoyl)-2-oxo-3-pyrrolidinyl-chloroacetate and cleaving off the chloroacetyl group from the latter or converting the (R)-4-(p-methoxybenzoylamino)-2-hydroxybutyric acid by means of trifluoroacetic acid anhydride into (R)-1-(p-methoxybenzoyl)-2-oxo-3-pyrrolidinyl-trifluoroacetate and cleaving off the trifluoroacetyl group from the latter.

Compounds of formula II in which $R^{11}$ and $R^{21}$ represent hydrogen and $R^{31}$ represents a protecting group, i.e. compounds of formula IIb, can be prepared, for example, by cyclising a compound of the general formula

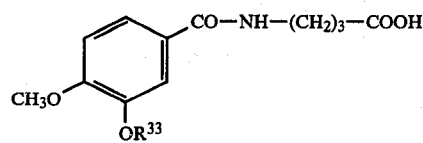

wherein $R^{33}$ has the significance given earlier.

In this cyclisation one mol of water is cleaved off and there are therefore used for this cyclisation methods which are generally customary for such dehydrating cyclisations, preferably treatment with a water-cleaving agent such as lower alkanecarboxylic acid anhydrides (e.g. acetic acid anhydride), substituted acetic acid anhydrides, thionyl chloride, polyphosphoric acid and the like and/or heating. Compounds of formula V, in turn, are obtained, for example, by acylating 4-aminobutyric acid with a sufficiently reactive derivative (especially a reactive halide, preferably the chloride) of an acid of the general formula

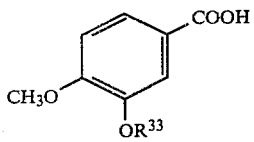

wherein $R^{33}$ has the significance given earlier.

Acids of formula VI hereinbefore and reactive derivatives thereof (for example, 3-benzyloxy-4-methoxybenzoyl chloride) are known or are readily accessible according to methods known per se.

Compounds of formula IIb can also be prepared by appropriately acylating 2-pyrrolidinone in the 1-position, there being used as the acylation agent a sufficiently reactive derivative (especially a reactive imidazolide or halide, preferably the chloride) of an acid of formula VI. The acylation of 2-pyrrolidinone with the chloride of an acid of formula VI is conveniently carried out in the presence of an inert organic solvent and a base. Especially suitable solvents are ethers such as diethyl ether, tetrahydrofuran, dioxan etc, aromatic hydrocarbons such as toluene etc or the like and especially suitable bases are tertiary amines such as triethylamine or the like. The acylation can also be carried out in pyridine which simultaneously functions as the solvent and as the base. Furthermore, the 2-pyrrolidinone can be treated firstly with a base capable of removing the hydrogen atom on the nitrogen atom in the 1-position and then reacted with the chloride of an acid of formula VI. In this embodiment there can be used as the base, for example, an alkali metal hydride such as sodium hydride or the like and as the solvent an aromatic hydrocarbon such as benzene, dimethylformamide or the like. It is also possible to use the 2-pyrrolidinone in the form of a reactive derivative in which a readily cleavable group, for example a readily cleavable metal-organic group, especially a trialkylsilyl group, is present on the nitrogen atom in the 1-position a preferred derivative being 1-trimethylsilyl-2-pyrrolidinone.

Furthermore, compounds of formula IIb can also be prepared by treating a compound of the general formula

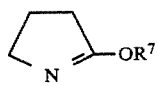

wherein $R^7$ represents lower alkyl,
with a halide of an acid of formula VI, whereupon the resulting intermediate is hydrolysed without isolation. In this procedure for the preparation of compounds of formula IIb a N-acylated lactam is prepared via a N-acylated enol ether, and methods for this are known per se. The preparation of the N-acylated enol ether is carried out in a suitable organic solvent such as benzene or the like and, if desired, in the presence of a strong base, for example in the presence of an alkali metal hydride such as lithium hydride. Depending on the reaction conditions used in the preparation of the N-acylated enol ether and its hydrolysis there can be obtained, in addition to the desired N-acylated lactam (i.e. in the present case the compound of formula IIb) in varying amounts also the corresponding amidoalkyl ester which results by ring-opening. Where the N-acylated enol ether is prepared in a solvent which is not miscible with water, then in the hydrolysis the formation of the desired product (i.e. the compound of formula IIb) predominates. The N-acylated enol ether is, as mentioned not collected, but is hydrolysed directly. The hydrolysis can be carried out in a manner known per se by adding water, aqueous alkali (e.g. lithium hydroxide solution) or aqueous acid (e.g. aqueous hydrochloric acid). It will be appreciated that in the foregoing procedure starting from compounds of formula VII there can be prepared only compounds of formula IIb in which $R^{33}$ represents a protecting group which is not affected in the hydrolysis of the N-acylated enol ether.

Compounds of formula II in which $R^{11}$ represents a protected hydroxy group and $R^{21}$ and $R^{31}$ represents hydrogen, i.e. compounds of formula IIc, can be prepared, for example, by appropriately acylating a pyrrolidine derivative of the general formula

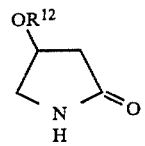

wherein $R^{12}$ has the significance given earlier,
in the 1-position, i.e. replacing the hydrogen atom in the 1-position of a compound of formula VIII by a p-methoxybenzoyl group. This can be carried out in an analogous manner to that described earlier in connection with the preparation of compounds of formula IIa by appropriately acylating pyrrolidine derivatives of formula IV. The compounds of formula VIII are known or are readily accessible according to methods known per se, especially from 4-hydroxy-2-pyrrolidinone by introducing the desired protecting group.

On the other hand, it is also possible to prepare compounds of formula IIc from 4-(p-methoxybenzoylamino)-3-hydroxybutyric acid which, in turn, can be obtained by appropriately acylating 4-amino-3-hydroxybutyric acid (for example, by means of p-methoxybenzoyl chloride). Thus, for example, by treating 4-(p-methoxybenzoylamino)-3-hydroxybutyric acid with hexamethyldisilazane there is effected in one operation cyclisation and introduction of the protecting group, i.e. there is obtained a compound of formula IIc in which $R^{12}$ represents trimethylsilyl.

The compounds of formula IIc have an asymmetric carbon atom in the 4-position of the 5-membered heterocycle. The relevant stereochemical relationships determine the stereochemical relationships in the compound of formula I in which $R^1$ represents hydroxy and $R^2$ and $R^3$ represent hydrogen, i.e. 1-(p-methoxybenzoyl)-4-hydroxy-2-pyrrolidinone, which can be manufactured from the compounds of formula IIc. The stereochemical relationships in the 4-position of the 5-membered heterocycle of the compounds of formula IIc are, in turn, determined by the intermediates and/or methods used in the preparation of the compounds of formula IIc. It will be clear to any expert how, having regard to the relationships just described, optically active or racemic 1-(p-methoxybenzoyl)-4-hydroxy-2-pyrrolidinone can be manufactured in accordance with the invention.

Compounds of formula III in which $R^{32}$ represents a reductively cleavable protecting group are prepared starting from compounds of the general formula

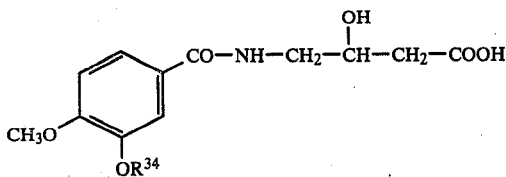

wherein $R^{34}$ represents a reductively cleavable protecting group,
by cyclisation and elimination, 2 mol of water being split off in one operation. The compounds of formula IX are accordingly subjected to methods which are generally customary for such water-cleavages, i.e. especially treatment with a suitable water-cleaving agent such as acetic anhydride or the like.

Compounds of formula III in which $R^{32}$ represents hydrogen are prepared by cyclisation with cleavage of 2 mol of water from compounds of the general formula

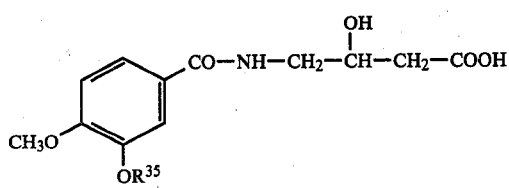

wherein $R^{35}$ represents a protecting group which is cleavable by non-reductive methods,
and subsequent cleavage of the mentioned protecting group. Suitable protecting groups denoted in formula X by $R^{35}$ are groups such as tert.butyl, fluorenecarbonyl, trialkylsilyl (e.g. trimethylsilyl) and the like; methods for the cleavage of such protecting groups are familiar to a person skilled in the art.

Compounds of formula IX and X, in turn, are obtained, for example, by acylating 4-amino-3-hydroxybutyric acid with sufficiently reactive derivatives of acids of the general formula

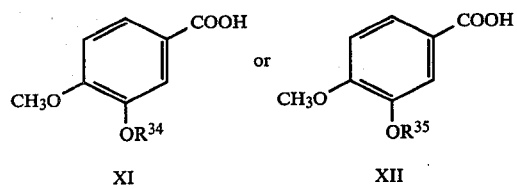

wherein $R^{34}$ and $R^{35}$ have the significance given earlier.

Reactive derivatives of acids of formulae XI and XII are known or are readily accessible according to generally usual methods.

As mentioned earlier, the pyrrolidine derivatives of formula I are novel compounds which have valuable pharmacodynamic properties. They have only a low toxicity and in the animal experiment described hereinafter, they demonstrate the capability of counteracting cerebral insufficiency produced experimentally.

POSTHYPERCAPNIC "AVOIDANCE" ACQUISITION

The test apparatus is a "shuttle box" having a 10 cm high hurdle in the middle and an electrifiable gird floor. A loudspeaker is mounted in the soundproof chamber. One or three hours after administration, by injection, of a control or test preparation, untrained rats (120–150 g; 10 per group) are placed for 12 seconds in a pure carbon dioxide environment. A third group of 10 rats is treated neither with the test preparation nor with carbon dioxide. Three minutes after treatment with carbon dioxide the rats of all three groups must learn a conditioned and unconditioned reflex in the "shuttle box" in the following programme: 10 seconds silence—5 seconds noise ("avoidance response")—15 seconds noise+foot-shock ("escape response"); six times in succession. For each of the six individual experiments the reaction time (time until the rat jumps over the hurdle) of each rat is measured and the statistical significance of the difference between the various groups is calculated by means of the Rang test.

An "active" dosage of a test preparation is that dosage which shows a significant activity during the six individual experiments; thereby the animals treated with the test preparation and carbon dioxide must learn significantly better than the animals treated only with carbon dioxide and equally well as the animals treated neither with the test preparation nor with carbon dioxide.

In the following Table there are compiled the dosages in which compounds of formula I exhibit a significant activity in this test; the Table also contains details concerning the acute toxicity of the compounds investigated (LD 50 in mg/kg in the case of single oral administration to mice).

| Compound | Significant active dosage | LD 50 |
|---|---|---|
| A | 3 mg/kg p.o. (after 1 hr.) | >5000 mg/kg p.o. |
| and | 10 mg/kg p.o. (after 1 hr.) | |
| A' | 30 mg/kg p.o. (after 1 hr.) | |
| B | 30 mg/kg p.o. (after 1 hr.) | 1250–2500 mg/kg p.o. |
| C | 10 mg/kg p.o. (after 1 hr.) | 2000–4000 mg/kg p.o. |

A: (R,S)-1-(p-Methoxybenzoyl)-3-hydroxy-2-pyrrolidinone
A': (R)-1-(p-Methoxybenzoyl)-3-hydroxy-2-pyrrolidinone
B: 1-(3-Hydroxy-4-methoxybenzoyl)-2-pyrrolidinone
C: (R,S)-1-(p-Methoxybenzoyl)-4-hydroxy-2-pyrrolidinone The compounds of formula I can be used as medicaments; for example, in the form of pharmaceutical preparations. The pharmaceutical preparations can be administered orally (e.g. in the form of tablets, coated tablets, dragées, hard and soft gelatin capsules, solutions emulsions or suspensions). They can, however, also be administered rectally (e.g. in the form of suppositories) or parenterally (e.g. in the form of injection solutions).

As mentioned earlier, medicaments containing a compound of formula I are also an object of the present invention as is a process for the manufacture of such medicaments, which process comprises bringing one or more compounds of formula I and, if desired, one or more other therapeutically valuable substances into a galenical administration form.

For the manufacture of tablets, coated tablets, dragées and hard gelatin capsules, the compounds of formula I can be administered with pharmaceutically inert, inorganic or organic excipients. As such excipients there can be used, for example, for tablets, dragées and hard gelatin capsules lactose, maize starch or derivatives thereof, talc, stearic acid or its salts etc. Suitable excipients for soft gelatin capsules are, for example, vegetable oils, waxes, fats, semi-solid and liquid polyols etc.

Suitable excipients for the manufacture of solutions and syrups are, for example, water, polyols, saccharose, invert sugar, glucose and the like.

Suitable excipients for injection solutions are, for example, water, alcohols, polyols, glycerine, vegetable oils etc.

Suitable excipients for suppositories are, for example, natural or hardened oils, waxes, fats, semi-liquid or liquid polyols and the like.

Moreover, the pharmaceutical preparations can contain preserving agents, solubilising agents, stabilising agents, wetting agents, emulsifying agents, sweetening agents, colouring agents, flavouring agents, salts for the variation of the osmotic pressure, buffers, coating agents or antioxidants. The pharmaceutical preparations can also contain still other therepeutically valuable substances.

In accordance with the invention, compounds of formula I can be used in the control or prevention of cerabral insufficiency, for example in the case of cerebral seizures, in geriatry, in alcoholism etc. The dosage can vary within wide limits and is, of course, fitted to the individual requirements in each particular case. In general, in the case of oral administration a daily dosage of about 10 mg to 2500 mg of a compound of formula I can be appropriate, although the upper limit quoted can be exceeded when this is shown to be indicated.

The following Examples are given by way of illustration of the present invention but are in no way intended to limit its extent.

EXAMPLE 1

(a) 15.8 ml of hexamethyldisilazane and 0.10 ml of trimethylchlorosilane are added to a suspension of 6.0 g of (R,S)-4-amino-2-hydroxy-butyric acid in 60 ml of anhydrous o-xylene. The mixture is heated to boiling for 4 hours while stirring and then evaporated, whereupon the residue is distilled. There is obtained (R,S)-3-(trimethylsilyloxy)-2-pyrrolidinone of boiling point 85°–87° C./0.02 mmHg and of melting point 35°–37° C.

(b) 5.0 g of (R,S)-3-(trimethylsilyloxy)-2-pyrrolidinone are placed in 130 ml of absolute tetrahydrofuran and 14.4 ml of a ca 2 molar solution of butyl lithium in hexane are added dropwise at −30° C. within 6 minutes. After stirring for 30 minutes at −30° C., 4.92 g of p-methoxybenzoyl chloride, dissolved in 10 ml of absolute tetrahydrofuran, are added dropwise at −30° C. during 5 minutes, whereupon the mixture is stirred at −30° C. for 3 hours and at room temperature for 1 hour. Thereupon, the mixture is evaporated and 30 ml of tetrahydrofuran and 6.7 ml of 1 N hydrochloric acid are added to the residue containing (R,S)-1-(p-methoxybenzoyl)-3-trimethylsilyloxy-2-pyrrolidinone. The mixture is stirred at room temperature for 7 minutes, cold water is then added thereto and the resulting mixture is extracted with ethyl acetate. The organic phase is dried over sodium sulphate and evaporated. The partially crystalline residue is stirred in a mixture of diethyl ether and ethyl acetate (3:1). After filtration and washing with the aforementioned mixture, there is obtained (R,S)-1-(p-methoxybenzoyl)-3-hydroxy-2-pyrrolidinone of melting point 124°–126° C.

EXAMPLE 2

(a) 14.0 g of 3-benzyloxy-4-methoxybenzoyl chloride are added in one portion at 26° C. to 15.6 g of 4-aminobutyric acid, 12.1 g of sodium hydroxide and 160 ml of ion-free water and subsequently 30 ml of tetrahydrofuran are added dropwise within 10 minutes. After 2 hours, the mixture is acidified with concentrated hydrochloric acid at a temperature below 10° C. The precipitate is separated and stirred with ethyl acetate. The mixture is filtered and the filter cake is washed with ethyl acetate. There is obtained 4-[(3-benzyloxy-4-methoxybenzoyl)amino]butyric acid which, after recrystallisation from ethyl acetate, melts at 156°–158° C.

(b) 2.0 g of 4-[(3-benzyloxy-4-methoxybenzoyl)amino]butyric acid are heated to reflux for 1 hour in 10 ml of acetic acid anhydride. After evaporation of the acetic acid anhydride, the residue is stirred at room temperature with diethyl ether. The mixture is filtered and the filter residue is washed with diethyl ether. There is obtained 1-(3-benzyloxy-4-methoxybenzoyl)-2-pyrrolidinone of melting point 92°–92° C.

(c) 2.0 g of 1-(3-benzyloxy-4-methoxybenzoyl)-2-pyrrolidinone are hydrogenated in 60 ml of absolute methanol with 0.5 g of 5% palladium/carbon under atmospheric pressure and at room temperature. The catalyst is filtered off and the filtrate is concentrated and stirred with diethyl ether. After filtration, there is obtained 1-(3-hydroxy-4-methoxybenzoyl)-2-pyrrolidinone of melting point 123°–125° C.

EXAMPLE 3

21.0 g of (R,S)-4-(trimethylsilyloxy)-2-pyrrolidinone are placed in 560 ml of absolute tetrahydrofuran and 60.6 ml of a 2 molar solution of butyl lithium in hexane are added dropwise at 0°− +5° C. After 30 minutes, 20.7 g of p-methoxybenzoyl chloride, dissolved in 30 ml of absolute tetrahydrofuran, are added dropwise at 0°− +5° C. within 10 minutes. The mixture is left to stand overnight in a refrigerator and is then evaporated. 140 ml of absolute tetrahydrofuran and 28 ml of 1 N hydrochloric acid are added to the residue containing (R,S)-1-(p-methoxybenzoyl)-4-trimethylsilyloxy-2-pyrrolidinone. The mixture is then stirred at room temperature for 7 minutes, ion-free water and ice are added thereto and the resulting mixture is extracted with ethyl acetate. The organic phase is washed with water, dried over sodium sulphate and evaporated. The residual oil is chromatographed over silica gel (granular size 0.2–0.5 mm). The (R,S)-1-(p-methoxybenzoyl)-4-hydroxy-2-pyrrolidinone, which is eluted with a mixture of methylene chloride and ethyl acetate (1:1), is crystallised from acetonitrile/ethyl acetate/isopropyl ether (1:3:1) and then has a melting point of 109.5°–111° C.

EXAMPLE 4

(a) 7.25 g of (R,S)-3-hydroxy-2-pyrrolidinone are dissolved in 140 ml of pyridine and 28 ml of chloroformic acid benzyl ester are added at 0°–5° C. Thereafter, the mixture is stirred at room temperature for 22 hours. The mixture is evaporated, the residue is stirred in toluene and the resulting mixture is evaporated. The residue is partitioned between ethyl acetate and water. The organic phase is washed with water and the aqueous phases are back-extracted with ethyl acetate. The combined ethyl acetate phases are dried over sodium sulphate and evaporated. The crystalline residue is stirred in 30 ml of diethyl ether and there is obtained (R,S)-3-(benzyloxycarbonyloxy)-2-pyrrolidinone of melting point 81°–82° C.

(b) 5.0 g of (R,S)-3-(benzyloxycarbonyloxy)-2-pyrrolidinone are silylated in tetrahydrofuran using trimethylchlorosilane and triethylamine. There is obtained (R,S)-3-(benzyloxycarboyloxy)-1-trimethylsilyl-2-pyrrolidinone of melting point 56°–58° C.

(c) 2.5 g (R,S)-3-(benzyloxycarbonyloxy)-1-trimethylsilyl-2-pyrrolidinone are mixed with 1.33 g of p-methoxybenzoyl chloride and the mixture is stirred at room temperature. Thereupon, the resulting trimethylchlorosilane is distilled off under reduced pressure in an oil-bath of 100° C. From the residue there is obtained, after crystallisation from diethyl ether, (R,S)-3-(benzyloxycarbonyloxy)-1-(p-methoxybenzoyl)-2-pyrrolidinone of melting point 123°–124° C.

(d) 0.10 g of (R,S)-3-(benzyloxycarbonyloxy)-1-(p-methoxybenzoyl)-2-pyrrolidinone is hydrogenated with hydrogen in 20 ml of tetrahydrofuran over 0.10 g of 5% palladium/carbon at atmospheric pressure. The catalyst is filtered off and the filtrate is concentrated, there being obtained (R,S)-1-(p-methoxybenzoyl)-3-hydroxy-2-pyrrolidinone which, after recrystallisation from ethyl acetate/n-hexane (1:2), melts at 124.5°–126° C.

EXAMPLE 5

(a) 17.2 g of p-methoxybenzoyl chloride are added while stirring well to 6.0 g of (R,S)-4-amino-2-hydroxybutyric acid and 150 ml of ion-free water. Thereafter, the mixture is adjusted to pH 10.5 with 2 N sodium hydroxide and stirred at room temperature for 70 minutes. The clear solution is treated with ice and adjusted to pH 1.4 with 25% hydrochloric acid. The separated solid is filtered off and washed with water. The filtrate is adjusted to pH 5.5 with sodium hydroxide and concentrated in a water-jet vacuum. The clear colourless solution is adjusted to pH 1.4 with 25% hydrochloric acid and extracted firstly with ether and then with ethyl acetate. The aqueous phases are adjusted to pH 5.5, concentrated, acidified with 25% hydrochloric acid and extracted with ethyl acetate. The combined ethyl acetate extracts are evaporated and the residue is recrystallised from ethyl acetate. There is obtained (R,S)-4-(p-methoxybenzoylamino)-2-hydroxy-butyric acid of melting point 127.5°–129.5° C.

(b) 3.0 g of (R,S)-4-(p-methoxybenzoylamino)-2-hydroxybutyric acid are heated at 145° C. for 30 minutes in 20 g of chloroacetic acid anhydride. The chloroacetic acid anhydride is distilled off in a high vacuum from the dark brown mixture. The residue is boiled in diisopropyl ether. The organic phase is decanted off and treated with charcoal. The clear colourless solution is cooled in an ice-bath and there is obtained (R,S)-1-(p-methoxybenzoyl)-2-oxo-3-pyrrolidinylchloroacetate of melting point 78°–80° C.

(c) 1.54 g of (R,S)-1-(p-methoxybenzoyl)-2-oxo-3-pyrrolidinylchloroacetate are heated at 100° C. in 50 ml of pyridine for 10 minutes under nitrogen with 0.42 g of thiourea and 7 ml of ethanol. The solvent is removed by evaporation and the residue is partitioned between ethyl acetate and water. The organic phase is washed several times with water and the aqueous phases are extracted with ethyl acetate. The combined ethyl acetate phases are evaporated, the residue is boiled at reflux in diisopropyl ether and then the solution is decanted off from insoluble constituents. The clear, colourless diisopropyl ether phase is stirred in an ice-bath and then left to stand in an ice box overnight. The product which crystallises out is filtered off and there is obtained (R,S)-1-(p-methoxybenzoyl)-3-hydroxy-2-pyrrolidinone of melting point 125°–126° C.

EXAMPLE 6

(a) 5.0 g of (R,S)-3-hydroxy-2-pyrrolidinone, 100 ml of dichloromethane and 39 ml of chloroacetyl chloride are boiled at reflux for 40 minutes while stirring. The mixture is then evaporated. The residue is stirred in diethyl ether and the mixture is filtered. The filter cake is recrystallised from ethyl acetate, there being obtained (R,S)-3-chloroacetoxy-2-pyrrolidinone of melting point 133°–134° C.

(b) 3.50 g of (R,S)-3-chloroacetoxy-2-pyrrolidinone and 7.5 ml of trimethylchlorosilane are dissolved in 200 ml of absolute tetrahydrofuran and 8.2 ml of triethylamine are added at −5° C. to 0° C. After stirring at 0° C. for 4 hours, the mixture is filtered. Control of the filtrate by NMR shows that the reaction is still not complete. After repeated reaction with trimethylchlorosilane, the filtrate contains 4.6 g of crude (R,S)-2-oxo-1-trimethylsilyl-3-pyrrolidinyl-chloroacetate. Purification is carried out by vacuum distillation; the distillate boils at 130° C./0.02 mmHg.

(c) 1.12 g of (R,S)-2-oxo-1-trimethylsilyl-3-pyrrolidinylchloroacetate and 0.76 g of p-methoxybenzoyl chloride are heated in an oil-bath of 100° C. for 30 minutes under nitrogen and while stirring. Towards the end of the reaction the resulting trimethylchlorosilane is distilled off under reduced pressure. The mixture is treated with diethyl ether, stirred at room temperature and filtered off. There is obtained (R,S)-1-(p-methoxybenzoyl)-2-oxo-3-pyrrolidinylchloroacetate of melting point 72°–73° C. which is pure according to thin-layer chromatography. The melting point does not increase after recrystallisation from diisopropyl ether.

(d) According to the procedure described in paragraph (c) of Example 5, from (R,S)-1-(p-methoxybenzoyl)-2-oxo-3-pyrrolidinyl-chloroacetate there is obtained (R,S)-1-(p-methoxybenzoyl)-3-hydroxy-2-pyrrolidinone of melting point 125°–126° C.

EXAMPLE 7

5.0 g of (R,S)-4-(p-methoxybenzoylamino)-2-hydroxy-butyric acid are boiled at reflux for 36 hours in 50 ml of trifluoroacetic acid anhydride and 1 g of sodium trifluoroacetate. The solvent is removed by evaporation and the resulting 1-(p-methoxybenzoyl)-2-oxo-3-pyrrolidinyl-trifluoroacetate (melting point 107°–108° C.) is boiled at reflux for 30 minutes in 50 ml of methanol. The mixture is then evaporated. The residue is partitioned between ethyl acetate and ion-free water. The constituents which are soluble in the ethyl acetate are stirred in 60 ml of a mixture of diethyl ether and ethyl acetate (3:1). After filtration, there is obtained crude (R,S)-1-(p-methoxybenzoyl)-3-hydroxy-2-pyrrolidinone of melting point 121°–124° C. After column chromatography on silica gel (granular size 0.2–0.5 mm), the (R,S)-1-(p-methoxybenzoyl)-3-hydroxy-2-pyrrolidinone, which is eluted with methylene chloride and methylene chloride/ethyl acetate (1:1), is stirred in diethyl ether and there is obtained a product of melting point 124.5°–126° C.

EXAMPLE 8

(a) 3.0 g of (R,S)-4-(p-methoxybenzoylamino)-2-hydroxy-butyric acid are heated to reflux for 15 minutes in 11 ml of acetic acid anhydride. The mixture is concentrated in a water-jet vacuum. Toluene is added thereto six times, the mixture being evaporated after each addition. The thus-obtained crude product is filtered through silica gel (granular size 0.2–0.5 mm). The product, which is eluted with methylene chloride, is distilled in a bulb-tube and there is obtained (R,S)-1-(p-methoxybenzoyl)-2-oxo-3-pyrrolidinylacetate of boiling point 186°–188° C./0.01 Torr.

(b) 0.86 g of (R,S)-1-(p-methoxybenzoyl)-2-oxo-3-pyrrolidinylacetate are treated in 43 ml of 0.05 molar potassium sodium phosphate buffer of pH 6.9 with 1080 units of esterase enzyme. The mixture is stirred at room temperature for 5.5 hours and then extracted with ethyl acetate. The ethyl acetate phase is washed with water. The aqueous phases are back-extracted with ethyl acetate. The combined ethyl acetate extracts are dried over sodium sulphate, filtered and evaporated. (R,S)-1-(p-methoxybenzoyl)-3-hydroxy-2-pyrrolidinone can be detected in the residue.

EXAMPLE 9

(a) 5.0 g of (R,S)-3-acetoxy-2-pyrrolidinone and 13.2 ml of trimethylchlorosilane are dissolved in 150 ml of absolute tetrahydrofuran and 14.7 ml of triethylamine are added dropwise at −5° C. to 0° C. while stirring. The mixture is stirred at 0° C. for 3 hours and then filtered. The filtrate is evaporated and the residue is distilled in vacuo. There is obtained (R,S)-2-oxo-1-trimethylsilyl-3-pyrrolidinylacetate of boiling point 120° C./0.02 mmHg.

(b) 1.0 g of (R,S)-2-oxo-1-trimethylsilyl-3-pyrrolidinylacetate and 0.77 g of p-methoxybenzoyl chloride are heated in an oil-bath of 100° C. for 45 minutes under nitrogen and while stirring; towards the end of the reaction the resulting trimethylchlorosilane being removed under reduced pressure. The oily residue is filtered through silica gel (granular size 0.2–0.5 mm). The (R,S)-1-(p-methoxybenzoyl)-2-oxo-3-pyrrolidinylacetate, which is eluted with methylene chloride, has a boiling point of 185°–190° C./0.01 mmHg.

(c) According to the procedure described in paragraph (b) of Example 8, from (R,S)-1-(p-methoxybenzoyl)-2-oxo-3-pyrrolidinylacetate there is obtained (R,S)-1-(p-methoxybenzoyl)-3-hydroxy-2-pyrrolidinone.

EXAMPLE 10

(a) 17.2 g of p-methoxybenzoyl chloride are added while stirring well to 6.0 g of (R)-4-amino-2-hydroxy-butyric acid and 150 ml of ion-free water. The mixture is then adjusted to pH 10.5 with 2 N sodium hydroxide and stirred at room temperature for 70 minutes. The clear solution is treated with ice and adjusted to pH 1.4 with 25% hydrochloric acid. The separated solid is filtered off and washed with water. The filtrate is adjusted to pH 5.5 with sodium hydroxide and concentrated in a water-jet vacuum. The clear colourless solution is adjusted to pH 1.4 with 25% hydrochloric acid and extracted firstly with ether and then with ethyl acetate. The aqueous phases are adjusted to pH 5.5, concentrated, acidified with 25% hydrochloric acid and extracted with ethyl acetate. The combined ethyl acetate extracts are evaporated and the residue is recrystallised from ethyl acetate. There is obtained (R)-4-(p-methoxybenzoylamino)-2-hydroxy-butyric acid of melting point 105°–106° C.; $[\alpha]_D^{20} = -12.4°$; $[\alpha]_{365}^{20} = -60.5°$ (c=1.0 in water). A further amount of (R)-4-(p-methoxybenzoylamino)-2-hydroxy-butyric acid of melting point 103.5°–104.5° C. can be isolated from the mother liquors.

(b) According to the procedure described in paragraph (b) of Example 5, from (R)-4-(p-methoxybenzoylamino)-2-hydroxy-butyric acid there is obtained (R)-1-(p-methoxybenzoyl)-2-oxo-3-pyrrolidinyl-chloroacetate; $[\alpha]_D^{20} = +116°$; $[\alpha]_{546}^{20} = +144°$; $[\alpha]_{365}^{20} = +717°$ (c=1 in chloroform).

(c) 5.0 g of (R)-1-(p-methoxybenzoyl)-2-oxo-3-pyrrolidinyl-chloroacetate are treated in pyridine with thiourea and ethanol according to the procedure described in paragraph (c) of Example 5; the reaction time amounting to 45 minutes. The residue obtained after working-up the ethyl acetate extracts is stirred in ether, the insoluble constituents being filtered off and recrystallised from diisopropyl ether. There is obtained (R)-1-(p-methoxybenzoyl)-3-hydroxy-2-pyrrolidinone of melting point 123°–124° C.; $[\alpha]_D^{20} = +214°$; $[\alpha]_{546}^{20} = +264°$; $[\alpha]_{365}^{20} = +1212°$ (c=1.0 in chloroform).

EXAMPLE 11

1.05 g of (R)-4-(p-methoxybenzoylamino)-2-hydroxy-butyric acid are boiled at reflux for 48 hours while stirring in 8.5 ml of trifluoroacetic acid anhydride and 0.2 g of sodium trifluoroacetate. After evaporation of the mixture, the residue is shaken twice with toluene and the toluene is then removed by evaporation in vacuo. The residue, containing (R)-1-(p-methoxybenzoyl)-2-oxo-3-pyrrolidinyl-trifluoroacetate, is boiled at reflux for 30 minutes in absolute methanol. After evaporation of the methanol, the residue is boiled in 400 ml of diisopropyl ether, the mixture is decanted, the solution is concentrated to 140 ml and then stirred at room temperature. The solid is filtered off and there is obtained (R)-1-(p-methoxybenzoyl)-3-hydroxy-2-pyrrolidinone of melting point 122.5°–123° C.; $[\alpha]_D^{20} = +207°$; $[\alpha]_{546}^{20} = +256°$; $[\alpha]_{365}^{20} = +1172°$ (c=1.0 in chloroform).

From the filtrate and the dichloromethane-soluble constituents of the constituents which are insoluble in diiospropyl ether there can be obtained by stirring in diethyl ether at room temperature additional (R)-1-(p-methoxybenzoyl)-3-hydroxy-2-pyrrolidinone of melting point 121°–122.5° C.; $[\alpha]_D^{20} = +200.3°$; $[\alpha]_{546}^{20} = +247.5°$; $[\alpha]_{365}^{20} = +1133.7°$ (c=1.0 in chloroform).

EXAMPLE 12

(a) 18.1 g of 4-amino-3-hydroxy-butyric acid are dissolved in 176 ml of 2 N sodium hydroxide. To this there are added within 2 minutes 14.0 g of 3-benzoyloxy-4-methoxybenzoylchloride and subsequently 30 ml of tetrahydrofuran. The mixture is stirred intensively at room temperature for 2 hours, then treated with ice and acidified with concentrated hydrochloric acid. The separated solid is filtered off and washed with water. After drying, the filter cake is boiled in ethyl acetate and the insoluble portion is recrystallised from tetrahydrofuran/n-hexane (3.6:1). There is obtained 4-[(3-benzyloxy-4-methoxybenzoyl)amino]-3-hydroxy-butyric acid of melting point 158°–160° C.

(b) 5.0 g of 4-[(3-benzyloxy-4-methoxybenzoyl)amino]-3-hydroxy-butyric acid are boiled at reflux for 20 minutes in 15 ml of acetic acid anhydride. After removal of the acetic acid anhydride by evaporation in vacuo, the residue is chromatographed on 20 g of silica gel (granular size 0.2–0.5 mm). The product mixture which is eluted with toluene and dichloromethane is separated by pressure chromatography on silica gel (granular size 0.063–0.2 mm). The almost pure 1-(3-benzyloxy-4-methoxybenzoyl)pyrrolin-2-one which is eluted with ethyl acetate/n-hexane (9:1) melts at 113°–114° C. after stirring in diethyl ether. The thin-layer chromatogram shows only one spot; the NMR spectrum agrees with the given structure.

(c) 150 mg of 1-(3-benzoyloxy-4-methoxybenzoyl)-pyrrolin-2-one are dissolved in 100 ml of ethyl acetate and hydrogenated with hydrogen over 150 mg of 5% palladium/carbon at atmospheric pressure. The catalyst is filtered off and the filtrate is concentrated. The residue is stirred at room temperature in diethyl ether. After filtration, there is obtained 1-(3-hydroxy-4-methoxybenzoyl)-2-pyrrolidinone of melting point 122°–124° C.

EXAMPLE 13

(a) By heating equimolar amounts of 3-benzyloxy-4-methoxybenzoyl chloride and 1-trimethylsilyl-2-pyrrolidinone in an oil-bath of 100° C. in analogy to the procedure described in paragraph (b) of Example 9 there is obtained 1-(3-benzoyloxy-4-methoxybenzoyl)-2-pyrrolidinone. After stirring in diethyl ether and recrystallisation from ethyl acetate/n-hexane (3:1), the substance melts at 90.5°–91° C.

(b) According to the procedure described in paragraph (b) of Example 2, from 1-(3-benzyloxy-4-methoxybenzoyl)-2-pyrrolidinone there is obtained 1-(3-hydroxy-4-methoxybenzoyl)-2-pyrrolidinone of melting point 123°–125° C.

EXAMPLE 14

(a) 10.7 g of (R,S)-4-amino-3-hydroxy-butyric acid and 7.2 g of sodium hydroxide are dissolved in 90 ml of ion-free water. 5.1 g of p-methoxybenzoyl chloride are added at 26° C. within 2 minutes while stirring, the temperature rising to 31° C. The mixture is stirred intensively at room temperature for 1 hour and then acidified with concentrated hydrochloric acid at an internal temperature of 5°–10° C. The separated solid is filtered off and washed with ion-free water until it has a weak acid reaction (pH about 4). There is obtained (R,S)-4-(p-methoxybenzoylamino)-3-hydroxy-butyric acid of melting point 119°–121° C. After concentration of the filtrate, there can be filtered off a further portion of the same product having the same melting point.

(b) 2.0 g of (R,S)-4-(p-methoxybenzoylamino)-3-hydroxy-butyric acid are boiled at reflux while stirring for 52 hours in 30 ml of o-xylene with 12 ml of hexamethyldisilazane and 0.10 ml of trimethylchlorosilane. The mixture is evaporated. Toluene is added four times the residue and the mixture is evaporated after each addition. The residue, containing (R,S)-1-(p-methoxybenzoyl)-5-oxo-3-trimethylsilyloxy-pyrrolidine, is stirred at room temperature for 2 hours in 20 ml of ethyl acetate and 15 ml of 0.4 N hydrochloric acid. The organic phase is washed with water. The aqueous phases are back-extracted with ethyl acetate. The combined organic phases are concentrated. The residue is chromatographed on silica gel (granular size 0.2–0.5 mm). The product which is eluted with ethyl acetate is again chromatographed on silica gel. The crude (R,S)-1-(p-methoxybenzoyl)-4-hydroxy-2-pyrrolidinone which is eluted with methylene chloride/ethyl acetate (1:1) is stirred at room temperature in diethyl ether. There is obtained a product of melting point 117°–119° C.

EXAMPLE A 1-(p-Methoxybenzoyl)-3-hydroxy-2-pyrrolidinone is used as the active substance for the manufacture of tablets of the following composition:

|  | Per tablet |
| --- | --- |
| Active substance (finely ground) | 25 mg |
| Lactose (powdered) | 180 mg |
| Maize starch (white) | 275 mg |
| Polyvinylpyrrolidone | 15 mg |
| Magnesium stearate | 5 mg |
|  | 500 mg |

The finely ground active substance, the powdered lactose and part of the white maize starch are mixed with another. The mixture is sieved, moistened with a solution of polyvinylpyrrolidone in water, kneaded, moist granulated and dried. The granulate, the rest of the maize starch and the magnesium stearate are sieved and mixed with one another. The mixture is pressed to tablets of suitable form and size.

EXAMPLE B 1-(p-Methoxybenzoyl)-3-hydroxy-2-pyrrolidinone is used as the active substance for the manufacture of tablets of the following composition:

|  | Per tablet |
| --- | --- |
| Active substance (finely ground) | 20 mg |
| Maize starch (white) | 220 mg |
| Lactose | 70 mg |
| Microcrystalline cellulose | 40 mg |
| Polyvinylpyrrolidone | 20 mg |
| Sodium carboxymethylstarch | 23 mg |
| Magnesium stearate | 2 mg |
|  | 395 mg |

The finely ground active substance, part of the white maize starch, the lactose, the microcrystalline cellulose and the polyvinylpyrrolidone are mixed with one another. The mixture is sieved and processed with the rest of the white maize starch and water to give a granulate which is dried and sieved. Then, the sodium carboxymethylstarch and the magnesium stearate are added thereto, mixed and the mixture is pressed to tablets of suitable size, which have a break-bar.

EXAMPLE C 1-(p-Methoxybenzoyl)-3-hydroxy-2-pyrrolidinone is used as the active substance for the manufacture of tablets of the following composition:

|  | Per tablet |
| --- | --- |
| Active substance (finely ground) | 125 mg |
| Maize starch (white) | 560 mg |
| Lactose | 165 mg |
| microcrystalline cellulose | 70 mg |
| Polyvinylpyrrolidone | 35 mg |
| Sodium carboxymethylstarch | 40 mg |
| Magnesium stearate | 5 mg |
|  | 1000 mg |

The finely ground active substance, part of the white maize starch, the lactose, the microcrystalline cellulose and the polyvinylpyrrolidone are mixed with one another. The mixture is sieved and processed with the rest of the white maize starch and water to give a granulate which is dried and sieved. Then, the sodium carboxymethylstarch and the magnesium stearate are added thereto, mixed and the mixture is pressed to tablets of suitable size, which have a break-bar.

EXAMPLE D 1-(p-Methoxybenzoyl)-3-hydroxy-2-pyrrolidinone is used as the active substance for the manufacture of duplex ampoules of the following composition:

| Active substance solution | | |
|---|---|---|
| Active substance | | 25 mg |
| Polyethyleneglycol | ad | 5 ml |
| Diluent | | |
| Water for injection | | 5 ml |

Prior to the injection the diluent is added to the content of the active substance ampoule. There are obtained 10 ml of a ready-for-use injection solution containing 25 mg of active substance.

EXAMPLE E 1-(p-Methoxybenzoyl)-3-hydroxy-2-pyrrolidinone is used as the active substance for the manufacture of duplex ampoules of the following composition:

| Active substance solution | | |
|---|---|---|
| Active substance | | 25 mg |
| Glycolfurol | ad | 3.5 ml |
| Diluent | | |
| Sodium chloride | | 67.5 mg |
| Water for injection | ad | 6.5 ml |

Prior to the injection the diluent is added to the content of the active substance ampoule. There are obtained 10 ml of a ready-for-use injection solution containing 25 mg of active substance.

EXAMPLE F 1-(p-Methoxybenzoyl)-3-hydroxy-2-pyrrolidinone is used as the active substance for the manufacture of duplex ampoules of the following composition:

| Active substance solution | | |
|---|---|---|
| Active substance | | 25 mg |
| Polyethyleneglycol | | 1.5 ml |
| Glycolfurol | ad | 4 ml |
| Diluent | | |
| Water for injection | | 6 ml |

Prior to the injection the diluent is added to the content of the active substance ampoule. There are obtained 10 ml of a ready-for-use injection solution containing 25 mg of active substance.

What is claimed:
1. A compound of the formula

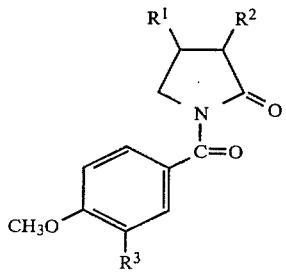

I wherein one of $R^1$, $R^2$ and $R^3$ represents hydroxy and the remaining substituents represent hydrogen.

2. (R)-1-(p-Methoxybenzoyl)-3-hydroxy-2-pyrrolidinone.
3. (R,S)-1-(p-Methoxybenzoyl)-3-hydroxy-2-pyrrolidinone.
4. (R,S)-1-(p-Methoxybenzoyl)-4-hydroxy-2-pyrrolidinone.
5. 1-(3-Hydroxy-4-methoxybenzoyl)-2-pyrrolidinone.
6. A compound of the formula

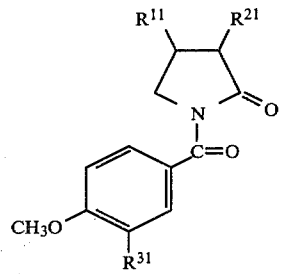

wherein $OR^{11}$ is a trialkylsilyl and $R^{21}$ and $R^{31}$ are hydrogen.

7. A compound of the formula

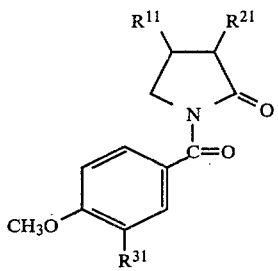

wherein $OR^{21}$ is selected from the group consisting of p-methoxytrityl, p,p'-dimethoxytrityl, p,p',p''-trimethoxytrityl, trialkylsilyl, hexahydropyran-2-yl, 4-methoxyhexahydropyran-4-yl, acetyl, chloroacetyl, trifluoroacetyl, methoxyacetyl, phenoxyacetyl, benzyloxycarbonyl, trichloroethoxycarbonyl, tribromoethoxycarbonyl and benzoylformyl and $R^{11}$ and $R^{31}$ are hydrogen.

8. A compound of the formula

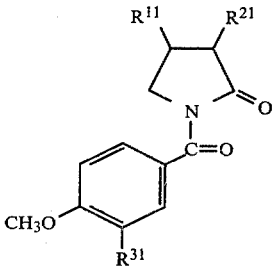

Wherein $OR^{31}$ is selected from the group consisting of tertiary butyl, benzyl, trialkylsilyl, hexahydropyran-2-yl, fluorenecarbonyl, benzyloxycarbonyl, trichloroethoxycarbonyl and tribromoethoxycarbonyl and $R^{11}$ and $R^{21}$ are hydrogen.

* * * * *